United States Patent
Opitz

(10) Patent No.: US 7,100,605 B2
(45) Date of Patent: Sep. 5, 2006

(54) THERAPY DEVICE FOR LOCAL TREATMENT OF COLDS

(75) Inventor: Christian Opitz, Tucson, AZ (US)

(73) Assignee: Vitaya Patent GmbH, Berlin (DE)

( * ) Notice: Subject to any disclaimer, the term of this patent is extended or adjusted under 35 U.S.C. 154(b) by 0 days.

(21) Appl. No.: 10/514,760

(22) PCT Filed: Apr. 25, 2003

(86) PCT No.: PCT/EP03/04340

§ 371 (c)(1),
(2), (4) Date: Nov. 17, 2004

(87) PCT Pub. No.: WO03/097143

PCT Pub. Date: Nov. 27, 2003

(65) Prior Publication Data

US 2005/0150501 A1 Jul. 14, 2005

(30) Foreign Application Priority Data

May 17, 2002 (EP) .................................. 02011080

(51) Int. Cl.
A61M 15/02 (2006.01)
(52) U.S. Cl. ........................ 128/202.25; 128/202.13; 128/204.17
(58) Field of Classification Search ............... 128/204, 128/202.13, 202.25, 204.17
See application file for complete search history.

(56) References Cited

U.S. PATENT DOCUMENTS

| 3,362,405 A | 1/1968 | Hazel |
| 4,549,051 A | 10/1985 | Ness |
| 5,038,769 A | 8/1991 | Krauser |
| 5,243,683 A | 9/1993 | Yang |

Primary Examiner—Henry Bennett
(74) Attorney, Agent, or Firm—D. Peter Hochberg; Sean Mellino

(57) ABSTRACT

The invention relates to a therapy device for the specifically local treatment and curing of colds in the region of the nose, frontal sinus and throat area in human beings. The external appearance of the therapy device can resemble that of a common hair dryer or face sauna, but the therapy device also contains a means for reducing or suppressing HF radiation (electrosmog) which is normally emitted towards the external environment. According to the invention, a body made of crystallized salt, especially from a natural source, resulting in negative ionization of the heated air flow, is arranged in the region of the heated air flow prior to the exit thereof from the small, handy device. The body is cross-flown by the heated air flow or is at least touched thereby. The treatment of colds with the aid of said therapy device is based on the fact that cold viruses, i.e., primarily rhino viruses and corona viruses, can be eliminated by active treatment with a heated air flow.

14 Claims, 5 Drawing Sheets

THERAPY DEVICE FOR LOCAL TREATMENT OF COLDS

CROSS REFERENCE TO RELATED APPLICATIONS

This application is a National Stage application of International Application No. PCT/EP03/04340, filed on Apr. 25, 2003, which claims priority of European application number 02 011 080.5, filed on May 17, 2002.

BACKGROUND OF THE INVENTION

1. Field of the Invention

The invention concerns a device for the treatment and cure of symptoms of illnesses caused by colds in humans, more particularly within the nasal cavities, the frontal sinuses and the throat region.

2. Description of the Prior Art

As a result of considerable virological research it has, already since about 1971, been accepted that the rhinovirus, which even then was known to be the cause of common colds, is not capable of replication at normal body temperatures of 37° C. Although all viruses causing infectious illnesses are cell specific, the rhinovirus was revealed to be unique by the fact that it can only exist within the epithelial layers of the nasal and throat passages, i.e. in body regions which, because of the inflowing air when inhaling, have a lower temperature than that of the inner body, and especially lower than the temperature of the human central body. The feasibility of curing common colds was not entertained at that time or at least not researched further in respect of any treatment processes, for the simple reason that it was not known what percentage of all colds were caused by either the rhinovirus or, as the case may be, the coronavirus. In the case of the latter type, it was likewise established that it was similarly sensitive to heat, in the same way as the rhinovirus.

In a study carried out in 1980 at the Harbord Hospital in Salisbury, England, Larson, Reed and Thyrell established that approximately 90% of all colds were caused by these two above-mentioned viruses, whereby the rhinovirus accounted for about 70% and the coronavirus for about 20%. Furthermore, it is known that the coronavirus consists of only two sub-types; whereas, at the moment there are 89 sub-types of the rhinovirus that have been categorised, and it is possible that there are several hundred additional sub-types still to be researched. It is important to realized that all sub-types of the rhinovirus and the coronavirus are incapable of survival at temperatures above 37° C. The human body itself makes use of the advantage of the susceptibility to heat of the rhino and corona viruses in its defense against colds. The typical epithelial swelling of the nasal cavities caused by the increased histamine production makes it impossible for a person suffering from a cold to breathe through the nose for the very reason that the body automatically tries to prevent the inflowing air from cooling the epithelium. The replication of the viruses is thereby retarded and within 3 to 4 days the production of interferon by the body attains a level which then makes it possible for the invasive viruses to be overcome. Normally, the regulation of the temperature of the nasal channels and the secondary nasal cavities is effected by means of the inflow of cool air and the discharge of heat via the brain. The closing of the nasal passages against inflowing air gives rise to the well-known and rather unpleasant over-heating of the brain. This explains the drowsiness that is felt by many people suffering from a cold.

The increased production of mucus is a further defence mechanism of the body in its attempt to rid itself of the virus. This process dehydrates the body by an unusually high amount of water being directed to the nasal passages. As a consequence of this dehydration, there is an increased accumulation of lactic acid and other "waste products" often causing pain to be felt across the whole body. However, in consideration of these reactions of the body to colds, it becomes apparent why conventional nasal sprays and other means that open the nasal passages temporarily are rather counter-productive and serve only to prolong the cold. The drying up of the mucus, the reduction of the swelling and the renewed inflow of cold air interferes with the defence mechanism of the body and thus increases the chances of survival of the viruses.

The above-mentioned discovery of the sensitivity to heat of the rhino and corona viruses led to various applications of heat in the treatment of colds. These made use of the knowledge that the above-mentioned viruses die off within minutes at air temperatures of between 50 and 53° C. Thus, certain so-called face saunas, for the isolated treatment of the head region, were developed for treating colds. Also, for a long time now, at least in Europe, dry saunas have been recommended by so-called holistic therapists.

From U.S. Pat. No. 4,699,136 a device is known which is constructed in the form of a hand-held hair dryer for the localised hypothermic treatment of colds whereby a heated air current of, for example, between 41 and 44° C., impinging the breathing region of the face, is additionally charged with a proportional amount of remedial medication that is admixed by means of a spray device.

Whilst these already disclosed therapies on repeated use are able to cause the symptoms of colds to disappear, they nevertheless have a few serious disadvantages. In the first place, any treatment in a dry sauna can normally only be endured once a day. However, it is impossible to kill all the viruses with just one application of hot air per day because, for one thing, incubated and crystallised viruses will then not be destroyed. Localised heated air hyperthermia using added aerosol-applied remedial medication is cost-intensive because of the comparatively large amount of remedial medication used and is almost never free of side effects. Dry saunas and steam inhalation can, in fact, afford some relief but never effect a cure. Inhalation of steam has the added disadvantage that it moistens the epithelium externally and thus prompts the body to reduce its own mucus production that serves as part of its defence. Face saunas and steam inhalations both have the disadvantage that that they cause the proportional distribution of Chi in the body. In other words, the equilibrium of biochemical and bioelectrical correlations can be thrown off-balance by overheating the whole of the head, and thus also, from the point of view of traditional Chinese holistic medicine, interfere with the Yin, in other words the fluid balance of the body, and reduce the effectiveness of blood-specific curative powers.

It is the task of the invention, on the basis of this briefly described technical background, to create a reasonably priced and easily manipulated device for the therapeutic treatment and cue of colds.

SUMMARY OF THE INVENTION

The invention achieves this task of a therapy device for the specifically local treatment of colds by means of an ionised heated current of air which is warmed up at least to the human central body temperature and acts directly and in a locally restricted manner via the nose onto the epithelium of the nasal cavities and the adjacent areas in the nasal/throat region with an easy to handle device into which a device for producing a current of air between a cold air intake site and a warm air discharge side and a controllable heating device for heating the current of air between the intake and the discharge side are incorporated and, by means of which a body containing crystallised salt on which a current of warm air impinges before discharge from the housing is replaceably held.

The means of which for ionisation of the warmed up current of air, the means for producing a heated current of air is preferably constructed as a hand-held device in the form of a hair dryer or as a table device with an essentially vertical heated air discharge and the body that is impinged by the thus generated heated air current is in the form of a matrix of the crystallised salt arranged within said current of air in different practical variants.

The body that consists of crystallised salt, or contains said salt, and is impinged by the heated air current can also be incorporated preferably so as to be replaceable, within an adaptor that is capable of being attached or clipped onto the table or hand-held appliance.

If the variant of a standing and/or table appliance which is presently preferred and has already been successfully tested is chosen, the therapeutic success can be increased and/or optimised during the treatment of a cold if a heated air flow guide adaptor is used whose heated air discharge aperture exhibits an edge contour which is matched to the nose area of the human face. In this way, it is possible to ensure in the nasal/throat region and the frontal sinuses that the epithelium of the nasal cavities and the adjacent areas, on the one hand, are impinged, on the one hand, by the optimum air temperature of e.g. 42° C. and, on the other hand, by an increased quantity of the ions resulting from the crystal salt over which the warm current of air flows. The temperature of the heated air flow can be adjusted in the region of 37° to approximately 54° and, in the case of a preferred appliance variant, maintained at a selected set value by a temperature control device.

The body containing the crystallised salt or formed by said salt can be constructed, for example, as a non-woven fabric filter pad filled with the natural crystal salt and/or containing said salt, or as a replaceable disc-shaped grid which contains the crystal salt in a more or less loosely packed form. For the design of the body of crystalline salt, there is a wide variety of different possibilities coming within the geometric constrictions imposed by the appliance producing the heat, i.e. more particularly the hairdryer or table appliance or the associated clip-on adaptor. In order to obtain as effective a release of the required negative ionised air ions in the heated air current as possible, the body of crystallised salt can—as previously mentioned—be a crystallised salt mixture that is permeable to air, the salt mixture being arranged so as to be replaceable and held in place, for example, by means of a grid-like encasement or a non-woven material. Experiments that are still being conducted have, however, also shown that a sleeve-shaped or ring shaped design of the body of crystallised salt can be sufficient or the desired pre-treatment of the heated current of air, whereby the crystallised salt body can be produced either die-pressed or preferably compression-cast as a moulded body together with a plastic component. Good results in respect of the desired ionisation of the heated air current are also achieved if the body of crystallised salt, when seen in the direction of the aircurrent, is constructed as a cylindrical sleeve having a tapered cross-section or, as the case may be, in particular having the form of a Laval nozzle, by means of which, in addition, a concentration and increase of the exit speed of the heated air current that has been ionised by the crystallised salt is obtained. Research and tests that have been carried out have shown that fundamentally, only a minimal contact of the heated air current with the crystallised salt is sufficient to obtain the desired effect of a negative ionisation at the same time as the intensification of the scalar wave field. It has also been shown to be appropriate to have a ring-shaped encasement that has been manufactured, more particularly and for example, as an injection-mould piece made of heat-resistant plastic and containing the salt as granular material and being replaceably attached as a non-woven fabric pad through which the heated air current passes, at or in the region of the opening and/of the adaptor.

Based on the above assertion that cold viruses, in principle, can be killed off by means of a heated current of air, the use of a conventional hairdryer could in fact be effective, according to the meaning of the above-mentioned hypothermic treatment, in eliminating the symptoms of a cold. However, during long-term application, this can have a negative effect on health and on a complete recovery. In this respect, it is important that hairdryers commonly produce electromagnetic fields in an order of magnitude of 700 mG. This value is far beyond the value of 30 mG considered to be safe by many specialists in the field. In this respect the fact must also be taken into consideration that the personal electromagnetic field of a person suffering from a cold has already become weakened because the body is making energy available for the healing process—a process which is generally considerably more complex than the elimination of the colds virus. The regeneration of the epithelium following a cold normally lasts between 40 and 60 days. This process could be severely interrupted, in the case of some persons, by any disturbance of the personal electromagnetic field caused by the electromagnetic fields of the hairdryer. Some children are particularly susceptible to high levels of electromagnetic field and general experience indicates that they become ill with colds about twice as frequently as adults. A further significant point is also that conventional hairdryers produce positive air ions (free radicals) in the air that they expel. These are likewise considered by many physicians to be detrimental to health, in particular if the air discharged from the hairdryer is directly inhaled which, however, would be necessary to combat the cold. Moreover, positive ions in the air are capable of causing the body, in individual cases, to become susceptible to bacterial infections and thus limit the value of any treatment using heated air produced by conventional hairdryers.

The invention extends beyond this pure heated air therapy by means of at least one or more selective technical additional measures. On the one hand, the device generating the heated air current, i.e. in particular the already mentioned hairdryer or the table device is used in conjunction with a relatively small amount of crystallised salt which is connected with the heated air device in such a way that the heated air that is expelled passes over the salt and combines with it to form a more or less closely associated interaction, radical (in particular positive ions) being avoided in the current of air and as many negative ions as possible being generated or built up.

Although it is known, in principle, e.g. from U.S. Pat. No. 3,362,405, DE 1 036 470 A1, SU 17 48 328 A1 that surrounding air enriched with saline, in particular common salt particles, has a positive influence in fighting diseases of the cold, the special local therapy with hypothermisation, on the one hand, and build up of negative ions by introducing a charge of crystal salt into the heated air current according to the invention, on the other hand, is, in this combination, a completely new therapy device concept.

In respect of further details of the air-ionising additional measure, reference is made to the above-mentioned description, the attached patent claims and the following description of practical examples.

As an advantageous additional measure, the principle of a hairdryer having an unusually low production of electromagnetic fields is used. As such, hair-drying appliances are already known having a very low external emission of electromagnetic fields in the region of, for example, only 2 mG. These, for example, are manufactured and distributed by the company EMHHC (Electromagnetic Health Hazard Control) in Pacific Palisades, Calif., USA.

A hairdryer that has been equipped in accordance with the teaching of the invention, for the treatment of colds, in particular also one designed as a table device with a warm air discharge adaptor matched to the human facial contour in the nasal/mouth area could, of course, also be used merely as a warm air treatment device without the user thereby exposing him/herself to the effects of high levels of EMF.

The crystallised salt from natural sources that is to be used in accordance with the invention has been known, at least in Europe and for a few hundred years, by the name of "The Royal Salt" because its use was reserved exclusively for royal households. In its natural state, it amounts to only about 1% of the deposits occurring in salt mines, for example at Bad Reihenhall (DE) or in the salt mines near Krakow (PL) and is also known as the "Kings Rock Salt". In many salt mines, there are no occurrences of it at all. The chemical composition and the properties of the crystallised salt are quite amazing and exceed by far those of common salt or rock salt. Crystallised salt, as it is preferably intended to be used in conjunction with the invention, contains as a rule all 81 elements of which the human body consists. It produces a permanent equable energy field (Meißnerfeld) which, in particular, enables it to convert discoherent electromagnetic fields, for example caused by an AC driven appliances, to coherence. It is not least for this reason that nuclear wastes are deposited in old and no longer used salt mines containing crystallised salt. The normal characteristics of naturally occurring salt apply only partly in respect of the crystallised form for instance, a great amount of scalar waves—the type of wave by means of which all cells in the human body communicate—is created by an via this crystallised type of salt. In this way, the compensatory influencing effects of the crystallised salt reach deep down into the human body.

It has been observed that the ionising effect of salt, and in this case in particular of crystallised salt, aids the body during regeneration of the epithelium, whereby the effectiveness of the treatment is also extended to secondary bacterial infections. In this way, it is not only the acute symptoms caused by viral infection that are treated but, in addition, the recuperation and return to health of the primary and secondary nasal passages is generally assisted. In this way, a greater resistance to colds and other infections is thus effected and also thus the possibility of catching an infectious disease in the future is reduced.

BRIEF DESCRIPTION OF THE DRAWINGS

The invention and advantageous features are explained below in more detail with reference to the drawings in exemplarily embodiments. These show.

DETAILED DESCRIPTION OF THE INVENTION

Figure 1:
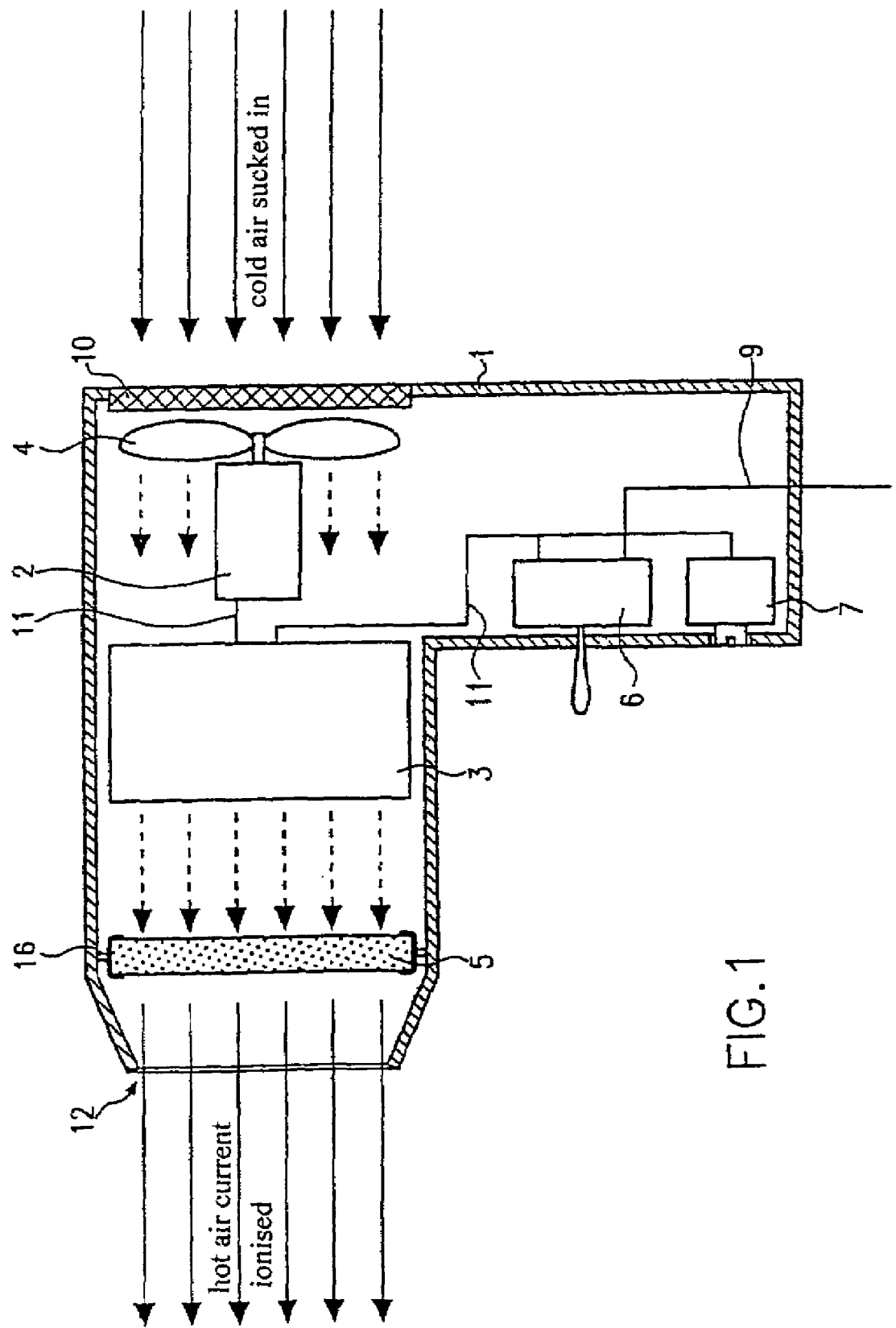
FIG. 1 is a sectional view representing the principle of a therapy device for the treatment of colds with features according to the invention.
Figure 2:
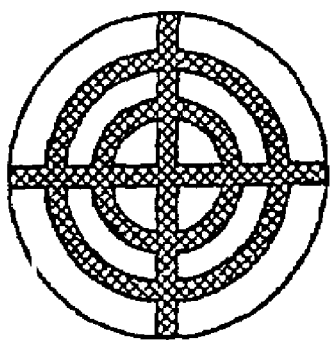
FIG. 2 to 6 are advantageous developmental arrangements of the body provided in accordance with the invention and constructed as a replaceable insert containing the crystallised salt or consisting of it and impinged by means of the heated air current prior to its emergence from the device.
Figure 3:
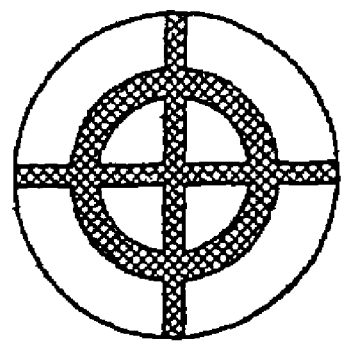
Figure 4:
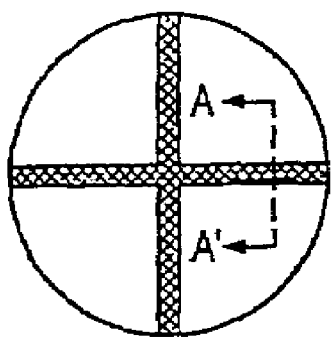
Figure 5:
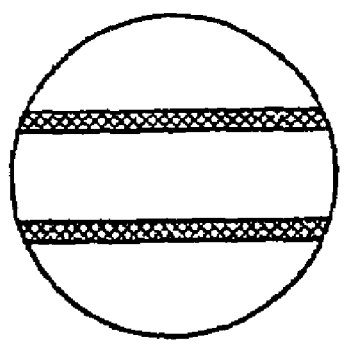
Figure 6:
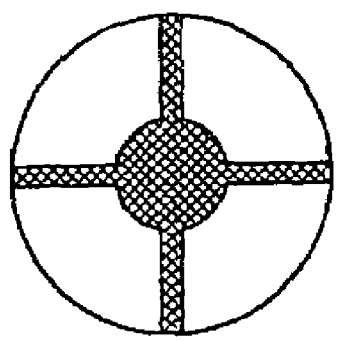

FIG. 1 shows the representational section view of the principle of a therapy device suitable for the treatment of colds in the constructional form as a hairdryer. Within an angular housing 1 that, basically for reasons of expense, as a rule is produced as an injection-moulded piece made of a dimensionally and thermally stable plastic, more particularly in fact the housing of a conventional hairdryer, are accommodated the following constructional groups or, as the case may be, parts—in each case represented in schematic form—in the indicated grouping, arrangement and reciprocal association: a blower motor 2 driving a bladed or propeller fan 4 by means of which cold ambient air is sucked in, preferably via a grating of a screen 10 located on the rear end (on the right hand side in the drawing). The inducted cold air flows through or across a heating element 3 in the form of a heating filament or rod or grid and is then, as a heated current of air, expelled via a front aperture 12 on the side opposite the intake side at a temperature of 37° C. to 54° C., preferably of 41° C. to 44° C. Arranged, in accordance with the invention, after the heating element 3 in the flow direction of the current air, there is a schematically indicated body 5 which consists of crystallised salt or contains a high proportion of said salt and is infiltrated or passed through or at least skimmed over by the heated current of air. As indicated in the drawing in FIG. 1, the body 5 can be constructed as a round, disk-shaped matrix element and arranged at right angles to the heated air current, whereby the expression "matrix element" signifies that salt crystals are mounted in a more or less loosely packed form within a grid-like, disk-shaped element, for example made of plastic, in particular a highly air-permeable non-woven material, and arranged in such a way that, in the course of the infiltration of the heated air, a more or less closely associated contact is made between the salt crystals and the infiltrating air. Another design possibility for the matrix element is to produce the salt crystals together with well-deformable plastic components as a disk-shaped, compression-moulded element that can be inserted so as to be replaceable in the foremost expulsion region of the heated air of the housing 1. A further possibility is to construct the body of crystallised salt or, as the case may be, embedded crystallised salt, in the form of a tubular sleeve that is incorporated so as to be replaceable within the foremost heated air expulsion region of the housing 1. This sleeve-shaped body, when seen in the flow direction of the current or air, can be constructed so as to the tapered on its air expulsion end, more particularly in the form of a Laval nozzle, by means of which good directional air flow and a closely associated contact of the infiltrating air with the crystallised salt is achieved, with the result that the desired good degree of negative ionisation of the heated air current can be obtained. Further examples of embodiments for a possible constructional design of the ionising body are illustrated by the schematic drawings of FIGS. 2 to 7, additional reference to which is made again below.

In the lower gripping region of the housing 1 a preferably multi-stage conventional line switch 6 is provided and, if need be, a line voltage selector switch 7. Reference number 9 denotes a power supply lead, the internal wiring within the device is indicated by means of reference number 11.

It is of particular advantage if the device generating the heated current of air produces as low an amount as possible of externally emitted electromagnetic fields. In order to achieve this, there are particularly a number of passive provisions that have already been disclosed, such as the use of HF filters, EM screening measures, the use of balanced circuit wiring and the like. A so-called resource element in the form of a geometric structure and information resonance key can also be provided by means of which the electromagnetic waves that are produced are modified into a nature-coherent form.

Figure 7:
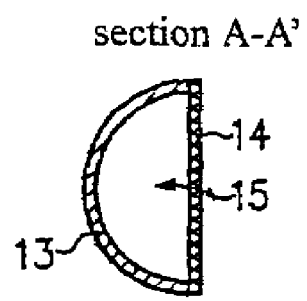
FIG. 7 is an enlarged representation of a sectional view seen in the direction of the arrows A–A' in FIG. 4.

If it is provided—as shown in FIG. 1—that the ionising body 5 made up of the crystallised salt should be arranged in the front expulsion region of the heated current of air, then there are various constructional possibilities that can be taken into consideration. Examples of this are shown in FIG. 2 to 6. In these examples the crystalline salt body is incorporated in a grid-like or cage-like plastic piece whose longitudinal and transverse ribs, as illustrated in FIG. 7, can be constructed as an injection-moulded piece 13 consisting of heat-resistant plastic, which is provided on a surface that is impinged by the inflowing current of air, said surface being on the reverse side of a cover that is permeable to air and consists, for example, of a plastic webbing 14. On the inside of this injection-moulded piece 13 that is covered by the plastic webbing 14 there is the crystalline salt 15. The whole structural component 5 in FIG. 1 is held in position, in such a way as to be replaceable, within the front air expulsion part of the device producing the heated air and it is secured, for example, by means of a clamping bracket 16.

Figure 8:
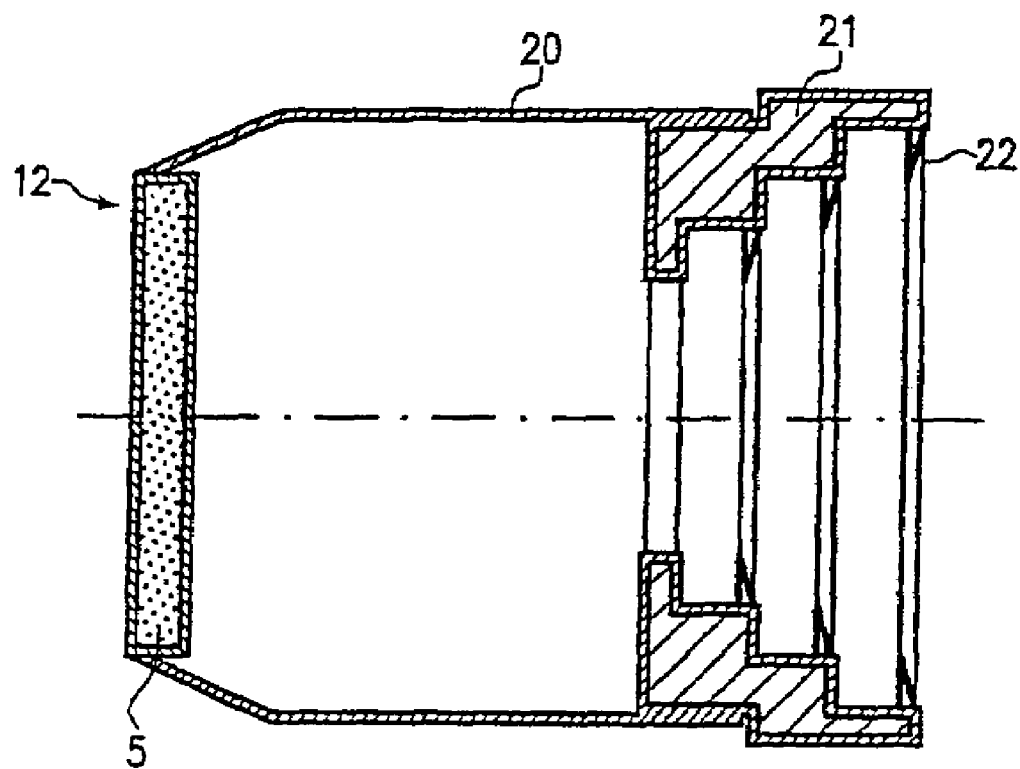
FIG. 8 is an auxiliary sleeve having an associated adaptor for the use of the invention when using a conventional hairdryer.
Figure 9:
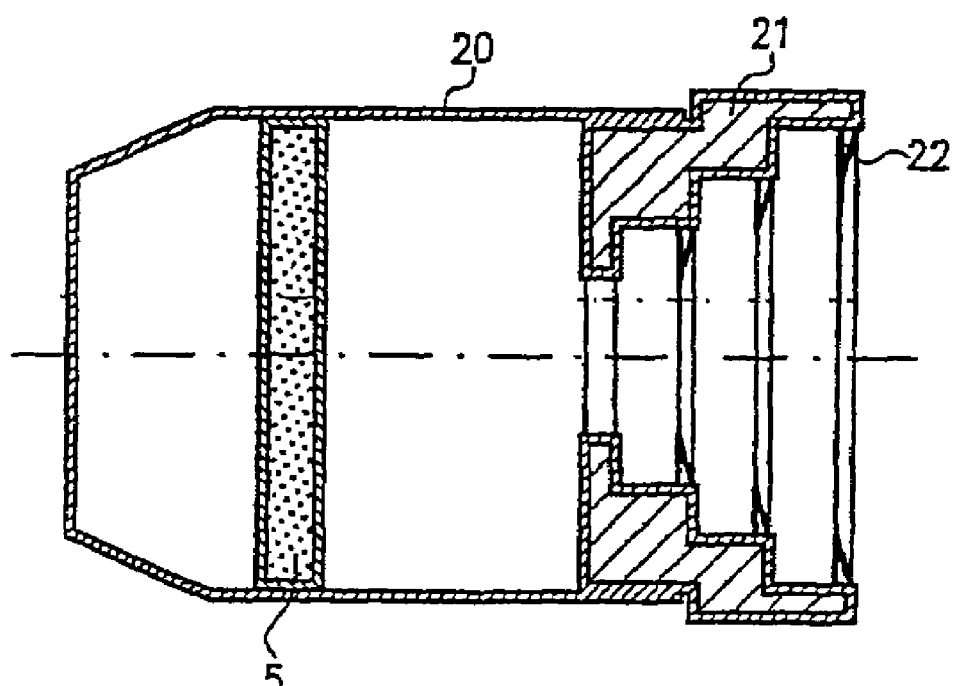
FIG. 9 is an alternative modified embodiment of the present invention, of an auxiliary sleeve having a salt-containing ionisation element and associated adaptor.

FIG. 8 and FIG. 9 illustrate two modified embodiments in which the ionising body 5 which is essential for the invention and is made up of crystalline salt or contains said salt, is held in position, likewise in such a ways as to be replaceable, in a separate top or front attachment 20. In the case of the embodiment variant in accordance with FIG. 8 the mounting of the body 5 is provided directly in the air expulsion aperture, whereas, in the case of the embodiment according to FIG. 9, the ionising element is arranged on the inside of the attachment 20. If necessary, an internally graduated adaptor ring 21 makes it possible for there to be a circumferential adjustment to different cross-sections of the air expulsion collar occurring in various types of hair-dryer. The various internal diameter graduations of the adaptor ring 21 can be provided with sealing lips 22 with the result that a highly airtight, secure mounting of the attachment 20 on the device producing the heated air is ensured.

Figure 10:
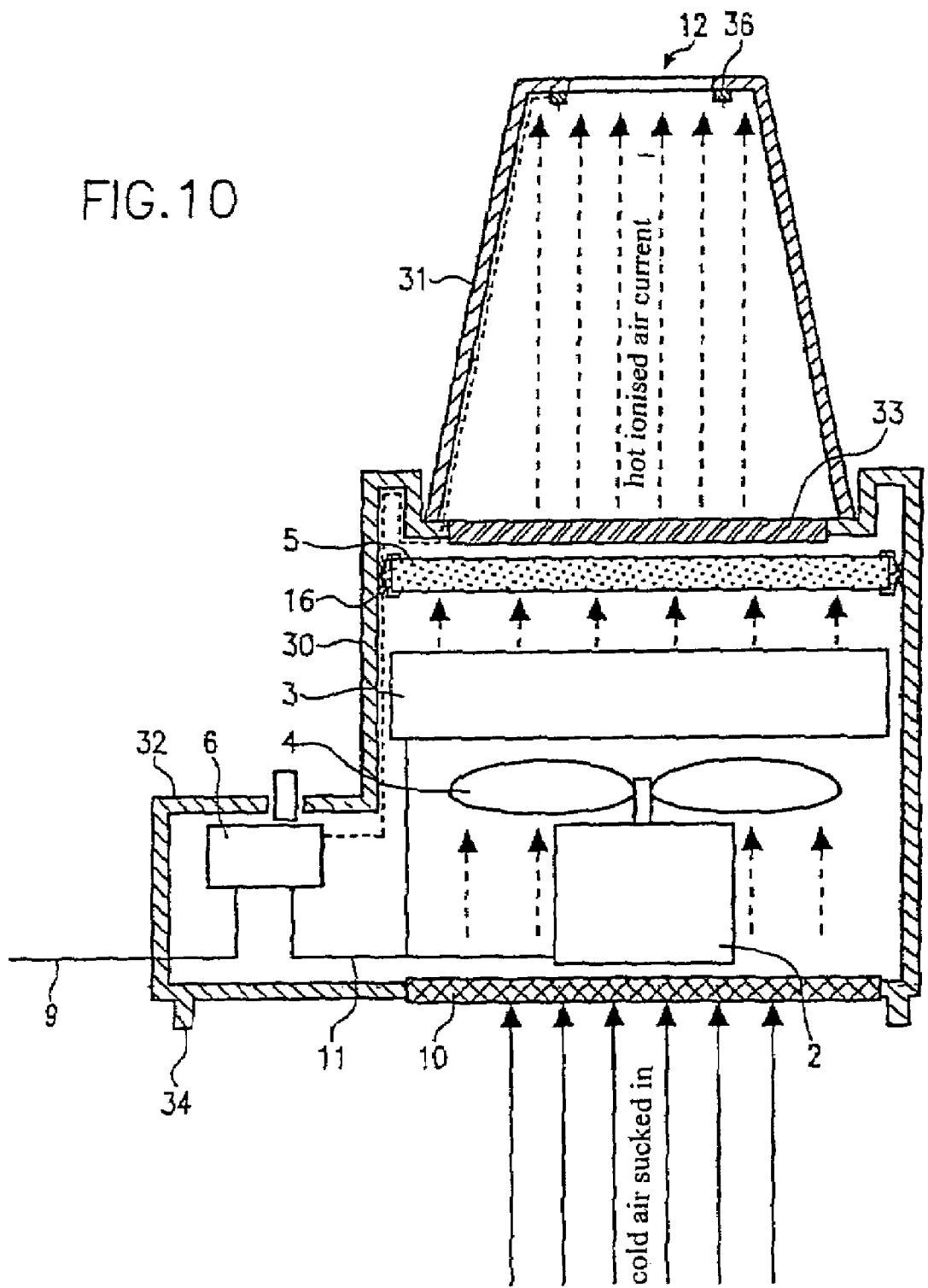
FIG. 10 is an embodiment adapted in line with the schematic representation of FIG. 1 of a therapy device according to the invention in a preferred design as a table device resembling a face sauna.

The diagrammatic sectional view of FIG. 10 illustrates an execution variant of the therapy device according to the invention which is to be placed on a horizontal surface, e.g. a table, which device in terms of its external form resembles a so-called face sauna which is known as such. The structural parts and structural modules known from the execution variant according to FIG. 1 are present also in this execution variant with basically the same function and at least a similar performance and indicated by the same reference such that a new description is superfluous to this extent. As can be seen, the design of the housing is different. This housing comprises, for example, a round base part 30 which, on its underside, is supported by slip-proof legs 34 such that a certain bottom clearance is provided so as not to impede the intake of the surrounding cold air via the sieve 10 fitted on the underside in this case and to keep the noise development as low as possible. In the sectional view of FIG. 10, on the left hand side, the base part 30 exhibits a radial bulge as operator's consol 32. The main switch 6 is advantageously combined with a time control such that a treatment time that can be preset, of e.g. two to maximum fifteen minutes can be preselected. The base part 30 exhibits on the upper surface a relatively large discharge opening for the air heated by the heating device 3, e.g. a PTC element. This air discharge aperture can be covered by a ventilation grid 33 as protection against contact. The air discharge aperture is enclosed and restricted by a clip-on part 31 in the shape of a hollow cone which can be removed, e.g. when the crystal salt load 5 held e.g. in an encasing non-woven material is to be replaced. The clip-on part 31 has an aperture 12 on its upper side through which the heated ionised current of air exits.

Figure 11:
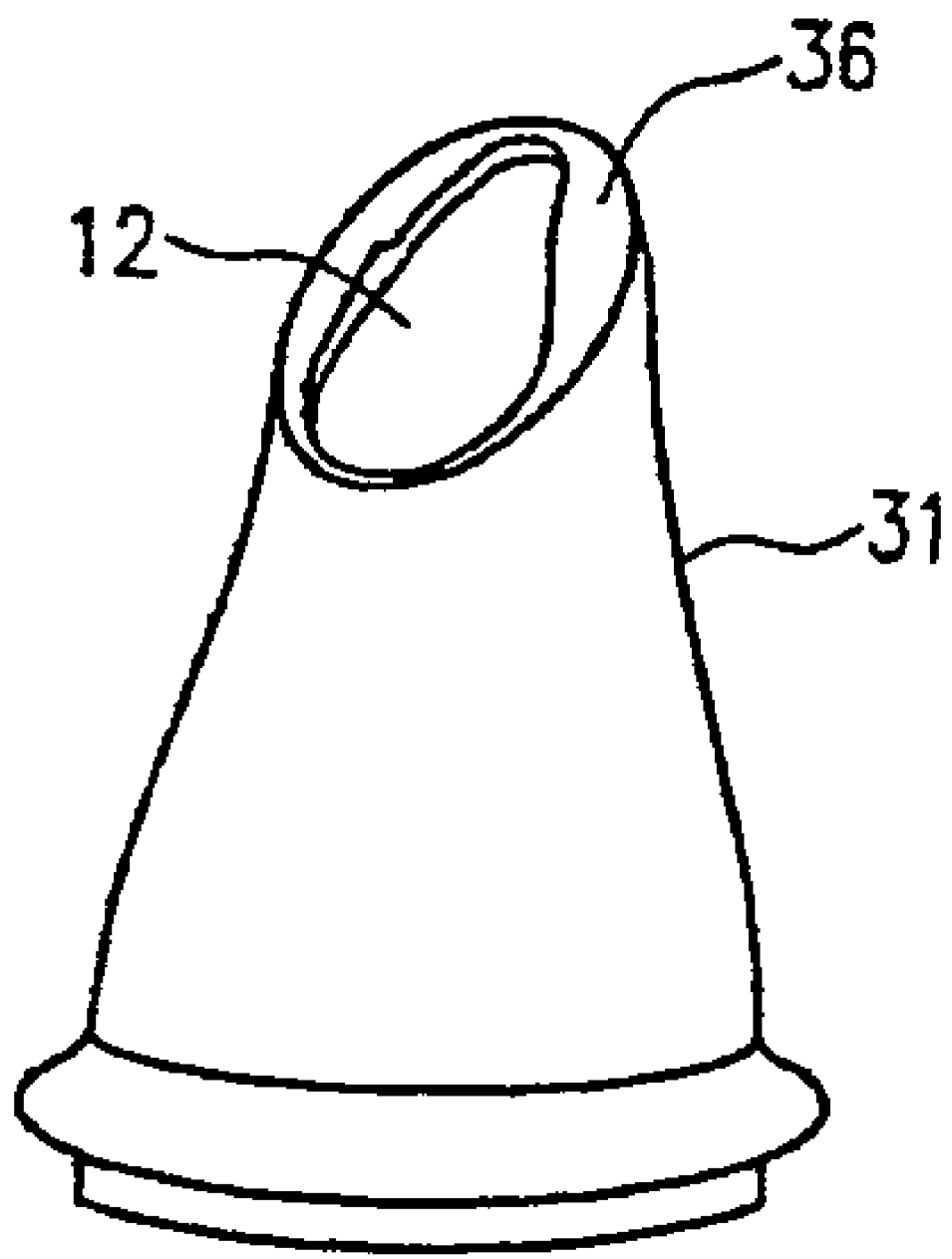
FIG. 11 is a diagrammatic representation, in perspective, of an upper housing part designed as a cone-shaped hollow clip-on part for the embodiment according to FIG. 10 with the edge of the warm air discharge aperture matched to the nose/upper lip part of the human face.

As shown in FIG. 11, the air discharge aperture exhibits a rounded edge whose contours are matched approximately to the contour of the lower nose/upper lip area of the human face such that as direct and local an effect of the ionised heated air current as possible via the two nostrils is optimally guaranteed. A heating output set-point selection can be provided on the operators' consol 32 e.g. in combination with the main switch 6, which set-point selection in turn is combined with a temperature control facility for the heated air current. For this purpose, at least one temperature sensor 36 can be provided in the area of the air discharge aperture 12, through which it is possible to guarantee that the discharge temperature of the air current is maintained at a predetermined treatment temperature in the region of e.g. 37° C. to 54° C., in particular in the optimum treatment region of approximately 41° C. to 44° C.

In order to make treatment with the therapy device according to the invention particularly effective, all the instructions briefly detailed below should be implemented.

It is, of course, best to begin the treatment on the first day of a cold. It is then possible to feel some improvement by the end of the same day. If, however, a cold has already been continuing for several days it can still be eliminated although it can take until the next morning before the onset of any real improvement.

If the nose is so congested that it is impossible to breathe through it, the very first use of the treatment will often open the nasal passages widely enough to solve the problem. In the event that this does not happen, a conventional nasal spray can be used to open the nasal passages. Breathing through the nose is absolutely necessary during the treatment. For this purpose the therapy device according to the invention is directed with the heated air expulsion end at the face, so that, if possible, only heated air is breathed in. The temperature setting and the distance to the face should result in the heat being felt altogether as unpleasant but still tolerable. It is advisable to keep a damp cloth ready on hand in order to avoid any extreme heating of the skin or indeed scorching. In order to obtain a cooling effect, it can also be appropriate to moisten the lips and the exterior of the nose, but only while breathing out. The process of breathing in the heated air should not be interrupted and so, if need be, the device can also be held a little further away in order to vary the temperature setting. If it is felt that the device has been set at an intolerably high temperature, it is best to start the treatment again from the very beginning. In this context hot air is inhaled exclusively for approximately 3 minutes, following which approximately 1.5 cups of warm water should be drunk, whereby "warm" means that the water can be swallowed without difficulty in normal mouthfuls and, more significantly, at intervals of 2 to 3 seconds. The water that is drunk should in no way have been heated up using microwave energy since this treatment destroys the natural structure of the water molecules which can lead to the formation of free radicals and radiolytic and radiomimetic toxic substances. This instruction is based particularly on the results of studies which show that water that has been heated by microwave can lead to an immune reaction which can conclusively be compared to those that arise as the result of an infectious illness. Such a reaction can last up to 8 hours with the result that, during an already existing infection, such as a cold, the immune system is subjected to even further strain, which, of course, would be counter-productive for the therapeutic treatment of the cold.

The whole process of inhaling for 3 minutes air that is exclusively hot and has been ionised by means of the therapy device in accordance with the invention, and of drinking 1.5 cups of hot water immediately afterwards, should be repeated five times. The intervals between these treatments should be at least one but not more that 1.5 hours. If these requirements are fulfilled, the results of experiments have shown that, in most cases, a full and complete recovery can be made. If, however, viruses are present that attain or have already attained a crystalline phase, it is not completely impossible for these crystallised viruses to survive even the high temperatures of the treatment. As a rule, in order actually to eliminate all the viruses, five applications using the therapy device are necessary, as previously mentioned, and in fact even if, for example after 3 of 4 treatment processes, the symptoms are already clearly receding. It is only after five applications that it can be assumed that even the incubated and crystallised viruses have, in most cases, been eliminated, with the result that there is no further possibility of the viruses reviving.

If a duly prescribed full treatment using the therapy device in accordance with the invention has not led to the complete disappearance of the symptoms of the cold within one day, then it must be assumed that something other than (only) a cold is wrong with the afflicted person. Because the respiratory system, in its reaction to illnesses, is somewhat restricted, a few other illnesses are capable of producing symptoms that are similar to a cold. If these symptoms persist, a doctor should be consulted.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

I claim:

1. A therapy device for the specifically local treatment of colds by an ionized heated current of air warmed up to at least the human central body temperature and acting directly and in a locally restricted manner via the nose onto the epithelium of the nasal cavities and the adjacent areas in the nasal/throat region with an easy to handle device, said therapy device comprising:
   a housing comprising:
      a cold air intake site;
      a warm air discharge side;
      a device for producing a current of air between said cold air intake site and said warm air discharge side;
      a controllable heating device for heating the current of air between said intake site and said discharge side to at least the human central body temperature; and
      a replaceable body containing crystallized salt, wherein the current of warm air impinges said body to ionize the heated current of air before being discharged from said housing directly in a locally restricted manner via a person's nose disposed in the ionized heated current of air, for flow onto the epithelium of the nasal cavities and the adjacent areas in the nasal/throat region of the person.

2. The therapy device according to claim 1, wherein said crystallized salt is obtained from natural deposits.

3. The therapy device according to claim 1, wherein said device housing has the form of a housing for a hairdryer and wherein said body impinged by the heated air current is a matrix comprising crystallized salt and arranged within said air current.

4. The device according to claim 1, wherein said device is a table device, and wherein said device housing further comprises a plurality of housing parts including a single-piece lower base part for supporting said therapy device on a support surface, wherein said lower base part contains the air current production device, the controllable heating device and a removeable hollow clip-on part having an upper heated air discharge opening joined on the upper side in an accurate fit to the base part and, wherein the body impinged by the heated air current contains a matrix comprising the crystallized salt arranged in the current of air, said therapy device further including an air-permeable envelope for fixing said body.

5. The therapy device according to claim 4, wherein the salt in the matrix is in the form of a relatively loosely packed measured quantity of crystalline salt, wherein said therapy device further comprises a replaceable disk-shaped grid or an air-permeable non-woven material positioned at right angles to the direction of the heated current of air for holding said body and said matrix in place.

6. The therapy device according to claim 3, wherein the matrix comprising crystallized salt is in the form of a tubular body arranged within the device in axial alignment to the heated current of air and is infiltrated by said heated current of air during the operation of the device.

7. The therapy device according to claim 6, wherein the tubular body is constructed in the form of a Laval nozzle in order to concentrate and increase the exit speed of the heated air current that has been ionised by the crystallized salt.

8. The therapy device according to claim 4, wherein the grid is an injection-molded piece comprising a heatproof plastic in the form of individual cross-linked hollow ribs, wherein the hollow ribs contain the crystallized salt mixture and, on the inflow side of the heated air current, are covered by a gauze comprising a heatproof plastic holding the salt mixture inside the hollow ribs.

9. The therapy device according to claim 4, wherein the base part is supported at the bottom by a plurality of slip-proof legs and includes a cold air inlet aperture on the bottom side and an outer projection designed as an operator's console.

10. The therapy device according to claim 4, wherein the clip on part comprises a hollow conical form and includes an upper side having an edge and a heated air discharge aperture on said upper side, said edge corresponding to the lower nasal/upper lip part of the human face.

11. The therapy device according to claim 1, wherein the controllable heating device is a PTC element.

12. The therapy device according to claim 1, wherein the heating device includes:

a time control device for operating said heating device, said time control device having a selectable time setpoint selection; and an adjustable performance control for adjusting the temperature of the heated air current and influencing said heating device.

13. The therapy device according to claim 12, further including a temperature sensor on the heated air outlet side for determining the performance control of the heating device.

14. The therapy device according to claim 1, wherein said device takes measurements for reducing electromagnetic fields of a higher frequency penetrating outwards (electrosmog).

* * * * *